United States Patent [19]

Bush et al.

[11] Patent Number: 4,654,159
[45] Date of Patent: Mar. 31, 1987

[54] ETHER HYDROXYPOLYCARBOXYLATE DETERGENCY BUILDERS

[75] Inventors: Rodney D. Bush; Stephen W. Heinzman, both of Cincinnati, Ohio

[73] Assignee: The Procter & Gamble Company, Cincinnati, Ohio

[21] Appl. No.: 754,560

[22] Filed: Jul. 11, 1985

Related U.S. Application Data

[63] Continuation-in-part of Ser. No. 748,529, Jun. 24, 1985, abandoned.

[51] Int. Cl.$^4$ .............. C11D 3/395; C11D 3/20; C07C 59/305
[52] U.S. Cl. ............... 252/95; 252/174.19; 252/174.24; 252/180; 252/DIG. 11; 560/180; 562/583
[58] Field of Search .............. 252/174.19, 174.24, 252/180, 95, DIG. 11; 560/180; 562/583

[56] References Cited

U.S. PATENT DOCUMENTS

| | | | |
|---|---|---|---|
| 3,635,830 | 1/1972 | Lamberti et al. | 252/174.19 |
| 3,692,685 | 9/1972 | Lamberti et al. | 252/174.19 |
| 3,769,223 | 10/1973 | Pearson et al. | 252/174.19 |
| 3,776,850 | 12/1973 | Pearson et al. | 252/174.19 |
| 3,954,858 | 5/1976 | Lamberti et al. | 252/132 |
| 3,970,698 | 7/1976 | Lannert | 562/583 |
| 4,011,264 | 3/1977 | House | 252/174.19 |
| 4,013,714 | 3/1977 | Lannert | 252/174.19 |
| 4,228,300 | 10/1980 | Lannert | 560/180 |
| 4,412,934 | 11/1983 | Chung et al. | 252/186.38 |
| 4,486,338 | 12/1984 | Ootani et al. | 252/545 |
| 4,524,009 | 6/1985 | Valenty | 252/89.1 |
| 4,537,706 | 8/1985 | Severson | 252/545 |
| 4,561,998 | 12/1985 | Wertz et al. | 252/547 |

FOREIGN PATENT DOCUMENTS

2408591 9/1975 Fed. Rep. of Germany .
186941 10/1984 Japan .

Primary Examiner—Prince E. Willis
Attorney, Agent, or Firm—Steven J. Goldstein; Jack D. Schaeffer; Edmund F. Gebhardt

[57] ABSTRACT

Ether hydroxypolycarboxylates prepared from epoxysuccinates by treatment with an alkaline calcium compound are disclosed. These compounds act as sequestering agents and are useful as detergency builders. Detergent compositions incorporating the ether hydroxypolycarboxylates can be prepared without use of detergent builder components containing phosphorus or nitrogen.

18 Claims, No Drawings

ETHER HYDROXYPOLYCARBOXYLATE DETERGENCY BUILDERS

This application is a continuation-in-part of co-pending U.S. patent application Ser. No. 748,529, filed June 24, 1985, now abandoned.

TECHNICAL FIELD

The present invention relates to ether hydroxypolycarboxylate compounds and a method for making them. The ether hydroxypolycarboxylates are effective sequestering agents and are useful in detergent compositions for household, institutional and industrial use.

BACKGROUND OF THE INVENTION

The role of sequestering agents in softening water by complexing the "hardness" cations in water supplies is well-known. Sequestering agents are recognized aids in detergent processes because they form a soluble complex with calcium and magnesium ions which can react with soaps and other anionic surfactants and otherwise adversely affect detergency. Polyphosphates such as tripolyphosphates and pyrophosphates are widely used as ingredients in detergent compositions in part because of their property of sequestering hardness ions. Such phosphorus-containing compounds as well as nitrogen-containing compounds, e.g., nitrilotriacetates, are highly effective. However, the effect of the phosphorus content and the nitrogen content of these sequestering agents upon eutrophication of lakes and streams has been questioned and the use of phosphates in detergent compositions has been subject to government scrutiny, regulation or prohibition.

These circumstances have developed a need for highly effective and efficient phosphorus-free and nitrogen-free sequestering agents and detergency builders.

The object of the present invention is to provide such a class of compounds which are useful as sequestering agents, especially when used as builders in detergent compositions containing surfactants.

U.S. Pat. No. 3,692,685, issued Sept. 19, 1972, to Lamberti et al. discloses detergent compositions containing an ether polycarboxylate having the formula:

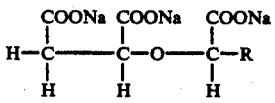

wherein R is H or —CH$_2$COONa

U.S. Pat. No. 4,228,300, issued Oct. 14, 1980, to Lannert, discloses ether polycarboxlate sequestering agents and detergency builders having the formula

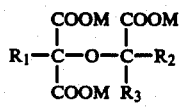

wherein M is alkali metal or ammonium, R$_1$ and R$_2$ are hydrogen, methyl or ethyl and R$_3$ is hydrogen, methyl, ethyl or COOM.

U.S. Pat. No. 3,769,223, issued Oct. 30, 1973, to Pearson et al. discloses 1-oxacyclopropane-2,3-dicarboxylic acid (i.e., epoxysuccinic acid) and its soluble salts as detergent builders.

U.S. Pat. No. 3,776,850, issued Dec. 4, 1973, to Pearson et al., discloses polymers to be used as detergent builders which are said to have the formula:

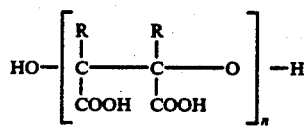

wherein R is hydrogen or other specified radicals and n is from 2 to about 40, preferably from 2 to about 6. The polymers are taught to be prepared by polymerization of the diethyl ester of 1-oxacyclopropane-2,3-dicarboxylic acid (i.e., epoxysuccinic acid) in the presence of a boron trifluoride catalyst followed by saponification. Detergent compositions are exemplified in which n is said to have an average value of approximately 3 or 4. In fact, the disclosed synthesis method yields mixtures of materials which contain very low levels of the n=3 and n=4 components.

It is a purpose of the present invention to provide: (1) new and superior ether hydroxypolycarboxylate sequestering agents based on epoxysuccinic acid or salts thereof, (2) detergent compositions containing said sequestering agents and (3) a method for making said sequestering agents.

More specifically, it is a purpose of the present invention to provide a process which produces a high yield of ether hydroxypolycarboxylates based on oligomers of epoxysuccinates or telomers of epoxysuccinates and tartrates, effective for sequestering multivalent metal cations.

SUMMARY OF THE INVENTION

The invention comprises metal sequestering agent compounds and mixtures of such compounds represented by the structure:

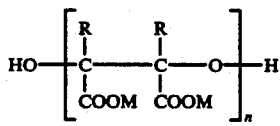

wherein M is hydrogen or a cation wherein the resultant salt is water soluble, preferably an alkali metal, ammonium or substituted ammonium cation, n is from about 2 to about 15 (preferably n is from about 2 to about 10, more preferably n averages from about 2 to about 4) and each R is the same or different and selected from hydrogen, C$_{1-4}$ alkyl or C$_{1-4}$ substituted alkyl (preferably R is hydrogen), provided that where there is a mixture at least about 25%, by weight, are compounds in which n is from about 2 to about 4, and further provided that said compounds or mixtures thereof have a log K$_{ca}$ (35° C., 0.1M ionic strength) of at least about 4.5 at pH 9.5.

Another aspect of the invention is detergent compositions containing from about 0.5% to about 98%, preferably from about 5% to about 30%, of a surfactant and from about 2% to about 99.5%, preferably from about 4% to about 50% of the metal sequestering agent compounds or mixtures defined hereinbefore or made by the process hereinbelow. The use of such detergent compositions in aqueous solutions for cleaning fabrics is also an aspect of the invention.

A preferred process for preparing the sequestering agent compounds of the invention comprises:

(1) oxidation of a maleate salt, which is optionally prepared from alkaline hydrolysis of maleic anhydride or a substituted maleate salt, such as a salt of citraconic acid, to an epoxysuccinate with the general structure

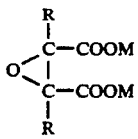

wherein M is a salt-forming cation, preferably alkali metal, and R is hydrogen, $C_{1-4}$ alkyl or $C_{1-4}$ substituted alkyl;

(2) treatment with at least about 5% of a molar quantity of calcium hydroxide, or other alkaline calcium salt, to form compounds of the general structure

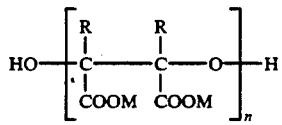

wherein M is a mixture of calcium and other alkaline-forming cations, preferably alkali metal, and n is from about 2 to about 15 and R is hydrogen, $C_{1-4}$ alkyl or $C_{1-4}$ substituted alkyl;

(3) replacement of calcium by alkali metal, such as sodium, or by ammonium, substituted ammonium or hydrogen can be accomplished by ion exchange; and (4) optional removal of tartaric acid and its salts (wherein n is 1) can be accomplished by solubilization (e.g., tartaric acid is soluble in acidic methanol, but not the sequestering agent compounds of the invention are not).

The invention also comprises metal sequestering agent compounds made by this process and detergent compositions containing such compounds.

It should be noted that, as used herein, "metal sequestering agent compounds" of the present invention includes mixtures of such compounds as long as they meet the specified size distribution and calcium binding constant limitations.

DETAILED DESCRIPTION OF THE INVENTION

The essential feature of the process of the invention and the sequestering agent compounds produced by this process is the use of calcium hydroxide or other alkaline calcium salts in the oligomerization of epoxysuccinates or in the telomerization of epoxysuccinates with tartrates or other hydroxyacids or salts thereof. The use of calcium as described herein promotes a high yield of the sequestering agent compounds of the invention when compared with, for example, the boron trifluoride catalyst used in the process disclosed in U.S. Pat. No. 3,776,850. The mixture of compounds produced by the process of U.S. Pat. No. 3,776,850 comprises compounds ineffective or relatively ineffective as sequestering agents and provides essentially no advantage over a monomeric epoxysuccinate.

One method of preparing the sequestering agent compounds of the invention comprises reacting a soluble epoxysuccinate with a molar equivalent quantity of calcium hydroxide in aqueous media, esterification of the resultant product, separation of the ester from the reaction mixture, and saponification of the ester to an alkali metal salt.

PROCESS EXAMPLE I

A more practical method of preparing a sequestering agent compound of the present invention comprises alkaline hydrolysis of maleic anhydride to a maleate salt, catalytic oxidization to an epoxysuccinate and then treatment with at least about 5%, preferably from about 10% to about 80%, of a molar equivalent amount of calcium hydroxide to form a mixture of alkali metal and calcium salts of the compounds of the present invention. An example follows:

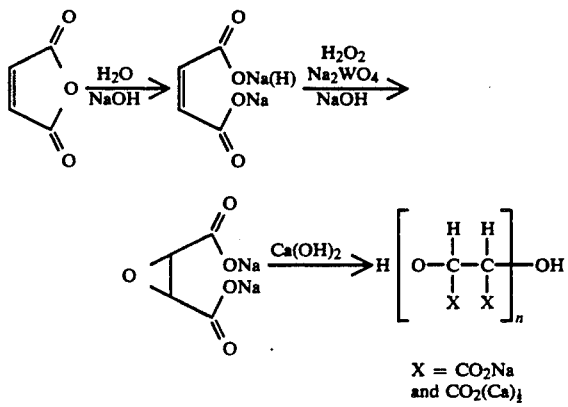

$X = CO_2Na$ and $CO_2(Ca)_{\frac{1}{2}}$

Maleic anhydride (22.3 g, 0.227 mol, F.W. 98) was dissolved in 32 mL of water and while this solution was cooled in an ice-bath, 29.3 g (50% soln., 0.34 mol) of sodium hydroxide solution was added. The resulting solution was placed in a 500 ml rounded bottom flask which was equipped with a magnetic stirring bar, pH probe, theromometer and an addition funnel. This reaction flask was then placed in an oil bath at 60° C. and when the reaction solution reached 55° C., 27 g of 30% hydrogen peroxide (0.238 mol) and 0.784 g (0.0024 mol) of sodium tungstate was added and the pH of the reaction solution maintained at 5–7 by addition of 9.1 g (50% solution, 0.224 mol) of sodium hydroxide. After about 40 minutes, an exotherm was noted (50° to 100° C.). The solution was allowed to cool to 60° C. and maintained at this temperature for an additional hour. Then 0.84 g (0.0114 mol) of calcium hydroxide was added to the reaction solution followed by heating to 100° C. for 2 hrs. A sample of the reaction solution indicated that a substantial amount of epoxysuccinate remained. 0.84 g (0.0114 mol) additional calcium hydroxide was added and the reaction heated to 100° C. for an additional 2 hrs. The volatiles were then removed by vacuum, and the resulting solid dried under vacuum at 100° C. for 16 hrs. to give 43.4 g of white solid which comprises a mixture of sodium and calcium salts of 2,6-dihydroxy-3,5-dicarboxy-4-oxa-1,7-heptanedioic acid (approx. 5%), higher molecular weight oligomers of epoxysuccinic acid and tartaric acid (approx. 20%).

Methylmaleic (citraconic acid) and other substituted cisbutenedioic acid compounds can be substituted for maleic acid in the foregoing reaction.

In one embodiment of the process d,l-tartaric acid or a salt thereof can be substituted for from about 10% to about 40%, preferably from about 15% to about 30%, of the epoxysuccinic acid or salt thereof on a molar basis. This substitution results in a higher yield of compounds wherein n has a value of 2 and a decreased amount of compounds wherein n has a value greater than 4. Tartaric acid salts present at the completion of the reaction can be recovered and recycled. Other hydroxycarboxylates such as glycolic, malic and gluconic acids can be substituted for tartaric acid in this embodiment of the process of the invention, but oligomerization of the epoxysuccinate tends to be the predominant reaction.

PROCESS EXAMPLE II

Disodium epoxysuccinate, disodium d,l-tartrate, calcium hydroxide and water were mixed in a molar ratio of 0.75: 0.25: 0.5:16. The mixture was maintained at 80° C. for 30 minutes.

The resultant product on a dry basis contained 70% oligomers of epoxysuccinic acid salts and 25% tartaric acid salts. Calcium was removed by acidification to pH 2 and use of an acid ion exchange poly (sulfonated styrene) resin. The oligomers were precipitated by addition of methanol at pH 2.5. The tartaric acid remained soluble. The polyepoxysuccinic acid (PESA) was converted to a sodium salt with NaOH.

The distribution of oligomers on a weight basis was determined to be approximately:

$n=2(51\%)$, $n=3(21\%)$, $n=4(16\%)$ and $n>4(13\%)$

A reduction in calcium hydroxide level from a 0.5 molar ratio level to a 0.1 molar level resulted in the following approximate distribution:

$n=2(22\%)$, $n=3(21\%)$, $n=4(21\%)$ and $n>4(35\%)$.

PROCESS EXAMPLE III

Disodium epoxysuccinate, calcium hydroxide and water were mixed in a molar ratio of 1.0:0.1:16. The mixture was maintained at 80° C. for 30 minutes.

The resultant product on a dry basis contained 93% oligomers of epoxysuccinic acid (PESA) and 7% tartaric acid salts.

The product can be used without further treatment as sequestering agent. Alternately, the calcium and tartaric acid can be removed as described in Process Example II, or by the precipitation of calcium ions with sodium carbonate, sodium silicate or similar materials.

The distribution of oligomers on a weight basis was determined to be approximately:

$n=2(8\%)$, $n=3(10\%)$, $n=4(13\%)$, $n>4(69\%)$

An increase in calcium hydroxide level from a 0.1 molar ratio level to a 0.25 molar level resulted in the following approximate distribution:

$n=2(20\%)$, $n=3-4(35\%)$, $n=3$ to $6(70\%)$, $n>6(10\%)$

CALCIUM BINDING CONSTANTS DETERMINATION

A computer system (Hewlett-Packard) with digital voltmeters was used to collect and analyze data from an Orion calcium selective electrode and a linear syringe buret (Sage Instruments syringe pump plus a linear potentiometer). An Analog Devices 40J non-inverting operational amplifier electrometer amplified the calcium electrode voltage and provided Nernstian behavior of the electrode into the $10^{-7}M$ range. Volumetric accuracy was better than $+/-0.5\%$.

Three hundred data pairs of [Ca total] vs $10^{(E/S)}$, which is a linear measure of [Ca free], were collected and corrected for diluton during each titration. S is the Nernst equation slope, ca. 29 mv/decade, and E is the calcium electrode voltage. Calcium ion was titrated into buffer solution. L represents the sequestering ligand. A ligand-free standard titration calibrated the electrode response. A second titration, containing a fixed concentration of total liquid [L tot] allowed calculation of $K_{Ca}$ at various [Ca tot]/[L tot] ratios.

$$K_{Ca} = \frac{[Ca\ tot] - [Ca\ free]}{[Ca\ free] \times [L\ free]}$$

where $[L\ free]=[L\ tot]-[Ca\ tot]+[Ca\ free]$

At high ratios of [Ca tot]/[L tot], the ligand became saturated with Ca ion and a linear increase in [Ca free] resulted. This line was extrapolated back to [Ca free]=0 and [Ca tot] at that point represented a measure of calcium binding capacity.

Ionic strength was 0.1M, [Ca tot]=0 to 1.4 mM (0 to 8.2 gr/gal), [Ligand total]=$3.52\times10^{-4}M$.

| Calcium Ion Binding Constants (35° C., 0.1 M ionic strength) | Log $K_{Ca}$ pH 9.5 |
|---|---|
| Material prepared by Process Example I | 5.2 |
| Product prepared by process disclosed in U.S. Pat. No. 3,776,850 | 3.0 |
| Nitrilotriacetic acid, sodium salt | 5.5 |
| 2-oxa-1,1,3 propanetricarboxylic acid, sodium salt | 4.3 |
| 2-oxa-1,3,4 butanetricarboxylic acid, sodium salt | 4.4 |
| Sodium tripolyphosphate | 4.9 |
| Sodium citrate | 3.5 |
| Sodium epoxysuccinate | 3.0 |

These results demonstrate a clear advantage in calcium binding for a sequestering agent compound of the present invention relative to prior art ether carboxylates and sodium citrate, a non-polymeric carboxylate sequestering agent used as a detergent builder material, as well as the material produced in U.S. Pat. No. 3,776,850. The compounds of the invention are approximately equivalent to sodium tripolyphosphate and sodium nitrilotriacetate in calcium binding, while being nitrogen and phosphorus-free.

DETERGENT COMPOSITIONS

Detergent compositions incorporating the sequestering agent compounds of the present invention contain as essential components from about 0.5% to about 98% of a surfactant and from about 2% to about 99.5% of the sequestering agent compounds of the present invention as a detergency builder.

Typical laundry detergent compositions within the scope of the present invention contain from about 5% to about 30% of a surfactant and from about 10% to about 80% total detergency builder, of which from about 20% to 100% by weight of total detergency builder components can be the sequestering agent compounds of the present invention.

The compositions of this invention are effective over the broad pH range of from about 6 to about 12. The compositions can be formulated to provide a desired pH by proper selection of the acid form of appropriate salts or mixtures thereof. Preferred water-soluble salts of the sequestering agent compounds are alkali metal salts such as sodium, potassium, lithium and ammonium or substituted ammonium, e.g. triethanol ammonium. Depending on the pH of the desired solution, the salts are partially or fully neutralized.

The detergent compositions of the invention can be prepared in solid or liquid physical form.

The detergent composition of the invention are particularly suitable for laundry use, but are also suitable for the cleaning of hard surfaces and for dishwashing.

In a laundry method aspect of the invention, typical laundry wash water solutions comprise from about 0.1% to about 1% by weight of the detergent compositions of the invention.

The Surfactant

The compositions of the invention contain from about 0.5% to about 98%, preferably from about 2% to about 30% by weight of a surfactant or mixtures thereof.

Various types of surfactants can be used in the compositions of the invention. Useful surfactants include anionic, nonionic, ampholytic, zwitterionic and cationic surfactants or mixtures of such materials. Detergent compositions for laundry use typically contain from about 5% to about 30% anionic surfactants or mixtures of anionic and nonionic surfactants. Detergent compositions for use in automatic dishwashing machines typically contain from about 2% to about 6% by weight of a relatively low sudsing nonionic surfactant or mixtures thereof and, optionally, suds control agents. Particularly suitable low sudsing nonionic surfactants are the alkoxylation products of compounds containing at least one reactive hydrogen wherein, preferably, at least about 20% by weight of the alkylene oxide by weight is propylene oxide. Examples are products of the BASF-Wyandotte Corporation designated Pluronic ®, Tetronic ®, Pluradot ® and block polymeric variations in which propoxylation follows ethoxylation. Preferred suds control agents include mono- and disteryl acid phosphates.

(A) ANIONIC SOAP AND NON-SOAP SURFACTANTS

This class of surfactants includes alkali metal monocarboxylates (soaps) such as the sodium, potassium, ammonium and alkylolammonium salts of higher fatty acids containing from about 8 to about 24 carbon atoms and preferably from about 12 to about 18 carbon atoms. Suitable fatty acids can be obtained from natural sources such as, for instance, from plant or animal esters (e.g., palm oil, coconut oil, babassu oil, soybean oil, castor oil, tallow, whale and fish oils, grease, lard, and mixtures thereof). The fatty acids also can be synthetically prepared (e.g., by the oxidation of petroleum, or by hydrogenation of carbon monoxide by the Fischer-Tropsch process). Resin acids are suitable such as rosin and those resin acids in tall oil. Naphthenic acids are also suitable. Sodium and potassium soaps can be made by direct saponification of the fats and oils or by the neutralization of the free fatty acids which are prepared in a separate manufacturing process. Particularly useful are the sodium and potassium salts of the mixtures of fatty acids derived from coconut oil and tallow, i.e., sodium or potassium tallow and coconut soap.

Soaps and fatty acids also act as detergency builders in detergent compositions because they remove multivalent ions by precipitation.

Anionic surfactants also include water-soluble salts, particularly the alkali metal and ethanolamine salts or organic sulfuric reaction products having in their molecular structure an alkyl radical containing from about 8 to about 22 carbon atoms and a sulfonic acid or sulfuric acid ester radical. (Included in the term alkyl is the alkyl portion of alkylaryl radicals.) Examples of this group of non-soap anionic surfactants are the alkyl sulfates, especially those obtained by sulfating the higher alcohols ($C_8$–$C_{18}$ carbon atoms); alkyl benzene sulfonates, in which the alkyl group contains from about 9 to about 15 carbon atoms, in straight chain or branched chain configuration, sodium alkyl glyceryl ether sulfonates; fatty acid monoglyceride sulfonates and sulfates; sulfuric acid esters of the reaction product of one mole of a $C_{12-18}$ alcohol and about 1 to 6 moles of ethylene oxide and salts of alkyl phenol ethylene oxide ether sulfate with about 1 to about 10 units of ethylene oxide per molecule and in which the alkyl radicals contain about 8 to about 12 carbon atoms.

Additional examples of non-soap anionic surfactants are the reaction products of fatty acids esterified with isothionic acid and neutralized with sodium hydroxide where, for example, the fatty acids are derived from coconut oil and sodium or potassium salts of fatty acid amide of methyl lauride in which the fatty acids, for example are derived from coconut oil.

Still other anionic surfactants include the class designated as succinamates. This class includes such surface active agents as disodium N-octadecylsulfosuccinamate; tetrasodium N-(1,2-dicarboxyethyl)-N-octadecylsulfosuccinamate; the diamyl ester of sodium sulfosuccinic acid; the dihexyl ester of sodium sulfosuccinic acid and the dioctyl ester of sodium sulfosuccinic acid.

Anionic phosphate surfactants are also useful in the present invention. These are surface active materials having substantial detergent capability in which the anionic solubilizing group connecting hydrophobic moieties is an oxy acid of phosphorus. The more common solubilizing groups are $-SO_4H$, $-SO_3H$, and $-CO_2H$. Alkyl phosphate esters such as $(R-O)_2PO_2H$ and $ROPO_3H_2$ in which R represents an alkyl chain containing from about 8 to about 20 carbon atoms are useful.

These esters can be modified by including in the molecule from one to about 40 alkylene oxide units, e.g., ethylene oxide units.

Particularly useful anionic surfactants useful herein are alkyl ether sulfates. The alkyl ether sulfates are condensation products of ethylene oxide and monohydric alcohols having about 10 to about 20 carbon atoms. Preferably, R has 12 to 18 carbon atoms. The alcohols can be derived from fats, e.g., coconut oil or tallow, or can be synthetic. Such alcohols are reacted with 1 to 30, and especially 3 to 6, molar proportions of ethylene oxide and the resulting mixture of molecular species, having, for example, an average of 3 to 6 moles of ethylene oxide per mole of alcohol, is sulfated and neutralized.

Other suitable anionic surfactants are olefin and paraffin sulfonates having from about 12 to about 24 carbon atoms.

(B) NONIONIC SURFACTANTS

Alkoxylated nonionic surfactants may be broadly defined as compounds produced by the condensation of alkylene oxide groups (hydrophilic in nature) with an organic hydrophobic compound, which may be aliphatic or alkyl aromatic in nature. The length of thee hydrophilic or polyoxyalkylene radical which is condensed with any particular hydrophobic group can be readily adjusted to yield a water-soluble compound having the desired degree of balance between hydrophilic and hydrophobic elements.

Alkoxylated nonionic surfactants include:

(1) The condensation product of aliphatic alcohols having from 8 to 22 carbon atoms, in either straight chain or branched chain configuration, with from about 5 to about 20 moles of ethylene oxide per mole of alcohol.

(2) The polyethylene oxide condensates of alkyl phenols, e.g., the condensation products of alkyl phenols having an alkyl group containing from about 6 to 12 carbon atoms in either a straight chain or branched chain configuration, with ethylene oxide, the ethylene oxide being present in amounts of from about 5 to about 25 moles of ethylene oxide per mole of alkyl phenol. The alkyl substituent in such compounds may be derived from polymerized propylene, diisobutylene, octene, or nonene, for example.

(3) Materials derived from the condensation of ethylene oxide with a product resulting from the reaction of propylene oxide and a compound with reactive hydrogen such as glycols and amines such as, for example, compounds containing from about 40% to about 80% polyoxyethylene by weight resulting from the reaction of ethylene oxide with a hydrophobic base constituted of the reaction product of ethylene diamine and propylene oxide.

Non-polar nonionic surfactants include the amine oxides and corresponding phosphine oxides. Useful amine oxide surfactants include those having the formula $R^1R^2R^3N-O$ wherein $R^1$ is an alkyl group containing from about 10 to about 28 carbon atoms, from 0 to about 2 hydroxy groups and from 0 to about 5 ether linkages, there being at least one moiety of $R^1$ which is an alkyl group containing from about 10 to about 18 carbon atoms and $R^2$ andd $R^3$ are selected from the group consisting of alkyl radicals and hydroxyalkyl radicals containing from 1 to about 3 carbon atoms.

Specific examples of amine oxide surfactants include: dimethyldodecylamine oxide, dimethyltetradecylamine oxide, ethylmethyltetradecylamine oxide, cetyldimethylamine oxide, diethyltetradecylamine oxide, dipropyldodecylamine oxide, bis-(2-hydroxyethyl)-dodecylamine oxide, bis-(2-hydroxypropyl)methyltetradecylamine oxide, dimethyl-(2-hydroxydodecyl)amine oxide, and the corresponding decyl, hexadecyl and octadecyl homologs of the above compounds.

(C) ZWITTERIONIC SURFACTANTS

Zwitterionic surfactants include derivatives of aliphatic quaternary ammonium, phosphonium, and sulfonium compounds in which the aliphatic moiety can be straight or branched chain and wherein one of the aliphatic substitutents contains from about 8 to 24 carbon atoms and one contains an anionic water-solubilizing group. Particularly preferred zwitterionic materials are the ethoxylated ammonium sulfonates and sulfates disclosed in U.S. Pat. Nos. 3,925,262, Laughlin et al, issued Dec. 9, 1975 and 3,929,678, Laughlin et al, issued Dec. 30, 1975, said patents being incorporated herein by reference.

(D) AMPHOLYTIC SURFACTANTS

Ampholytic surfactants include derivatives of aliphatic-heterocyclic secondary and tertiary amines in which the aliphatic moiety can be straight chain or branched and wherein one of the aliphatic substitutents contains from about 8 to about 24 carbon atoms and at least one aliphatic substituent contains an anionic water-solubilizing group.

(E) CATIONIC SURFACTANTS

Cationic surfactants comprise a wide variety of compounds characterized by one or more organic hydrophobic groups in the cation and generally by a quaternary nitrogen associated with an acid radical. Pentavalent nitrogen ring compounds are also considered quaternary nitrogen compounds. Suitable anions are halides, methyl sulfate and hydroxide. Tertiary amines can have characteristics similar to cationic surfactants at washing solutions pH values less than about 8.5.

A more complete disclosure of cationic surfactants can be found in U.S. Pat. No. 4,228,044, issued Oct. 14, 1980, to Cambre, incorporated herein by reference.

When cationic surfactants are used in combination with anionic surfactants and certain detergency builders including polycarboxylates, compatibility must be considered. A type of cationic surfactant generally compatible with anionic surfactants and polycarboxylates is a $C_{8-18}$ alkyl tri $C_{1-3}$ alkyl ammonium chloride or methyl sulfate.

More complete disclosures of surfactants suitable for incorporation in detergent compositions of the invention are in U.S. Pat. Nos. 4,056,481, Tate Nov. 1, 1977); 4,049,586, Collier (Sept. 20, 1977); 4,040,988, Vincent et al (Aug. 9, 1977); 4,035,257, Cherney (July 12, 1977); 4,033,718, Holcolm et al (July 5, 1977); 4,019,999, Ohren et al (Apr. 26, 1977); 4,019,998, Vincent et al (Apr. 26, 1977); and 3,985,669, Krummel et al (Oct. 12, 1976); all of said patents being incorporated herein by reference.

OPTIONAL DETERGENCY BUILDERS

The detergent compositions of the present invention can contain detergency builders in addition to the ether hydroxypolycarboxylate sequestering agent compounds described herein.

Suitable additional polycarboxylate detergency builders include the acid form and alkali metal, ammonium and substituted ammonium salts of citric, ascorbic, phytic, mellitic, benzene pentacarboxylic, oxydiacetic, carboxymethyloxysuccinic, carboxymethyloxymalonic, cis-cyclohexanehexacarboxylic, cis-cyclopentanetetracarboxylic and oxydisuccinic acids. Also suitable are polycarboxylate polymers and copolymers described in U.S. Pat. No. 3,308,067, Diehl, issued Mar. 7, 1967, incorporated herein by reference. Particularly suitable are acrylic acid polymers and salts thereof and copolymers of acrylic and maleic acids and salts thereof which act as dispersants of particulate materials in wash solutions.

The polyacetal carboxylates disclosed in U.S. Pat. No. 4,144,226 issued Mar. 13, 1979, to Crutchfield et al and U.S. Pat. No. 4,146,495 issued Mar. 27, 1979 to Crutchfield et al can be incorporated in the compositions of the invention.

Also suitable in the compositions of the invention are the 3,3-dicarboxy-4-oxa-1,6-hexanedioates and the related compounds disclosed in U.S. Ser. No. 672,302 filed Nov. 16, 1984, and incorporated herein by reference.

Suitable ether polycarboxylates also include cyclic compounds, particularly alicyclic compounds, such as described in U.S. Pat. Nos. 3,923,679; 3,835,163; 4,158,635; 4,120,874 and 4,102,903, incorporated herein by reference.

Polyphosphonate detergency builders comprise a large range of organic compounds having two or more $C-PO_3M_2$ groups, wherein M is hydrogen or a salt-forming radical. Suitable phosphonates include ethane-1-hydroxy-1,1-diphosphonates, ethanehydroxy-1,1,2-triphosphonates and their oligomeric ester chain condensates. Suitable polyphosphonates for use in the compositions of the invention also include nitrogen-containing polyphosphates such as ethylenediaminetetrakis (methylenephosphonic) acid and diethylenetriaminepentakis (methylenephosphonic) acid and alkali metal, ammonium and substituted ammonium salts thereof. In common with other phosphorus-containing components, the incorporation of phosphonates may be restricted or prohibited by government regulation.

As discussed hereinbefore $C_{8-24}$ alkyl monocarboxylic acid and soluble salts thereof have a detergent builder function in addition to surfactant characteristics. $C_8$-$C_{24}$ alkyl, alkenyl, alkoxy and thio-substituted alkyl dicarboxylic acid compounds, such as 4-pentadecene-1,2-dicarboxylic acid, salts thereof and mixtures thereof, are also useful optional detergency builders.

Inorganic detergency builders useful in the compositions of the invention at total combined levels of from 0% to about 75% by weight, include alkali metal phosphates, sodium aluminosilicates, alkali metal silicates and alkali metal carbonates.

Granular laundry detergent compositions generally contain at least about 40% of inorganic salts and it is desirable that a major portion of such salts provide a contribution to the detergent effect. Inorganic detergency builders are less useful in liquid detergent compositions of the invention and can be omitted to provide optimum physical properties and optimum levels of the essential components.

Phosphate detergency builders include alkali metal orthophosphates which remove multivalent metal cations from laundry solutions by precipitation and the polyphosphates such as pyrophosphates, tripolyphosphates and water-soluble metaphosphates that sequester multivalent metal cations in the form of soluble complex salts. Sodium pyrophosphate and sodium tripolyphosphate are particularly suitable in granular detergent compositions to the extent that governmental regulations do not restrict or prohibit the use of phosphorus-containing compounds in detergent compositions. Granular detergent composition embodiments of the invention particularly adapted for use in areas where the incorporation of phosphorus-containing compounds is restricted contains low total phosphorus and, preferably, essentially no phosphorus.

Crystalline aluminosilicate ion exchange materials useful in the practice of this invention have the formula $Na_z[(AlO_2)_z(SiO_2)_y]H_2O$ wherein z and y are at least about 6, the molar ratio of z to y is from about 1.0 to about 0.5 and x is from about 10 to about 264. In a preferred embodiment the aluminosilicate ion exchange material has the formula $Na_{12}[(AlO_2)_{12}(SiO_2)_{12}]xH_2O$ wherein x is from about 20 to about 30, especially about 27.

Amorphous hydrated aluminosilicate material useful herein has the empirical formula: $Na_z(zAlO_2 \cdot ySiO_2)$, z is from about 0.5 to about 2, y is 1 and said material has a magnesium ion exchange capacity of at least about 50 milligram equivalents of $CaCO_3$ hardness per gram of anhydrous aluminosilicate.

The aluminosilicate ion exchange builder materials herein are in hydrated form and contain from about 10% to about 28% of water by weight if crystalline and potentially even higher amounts of water if amorphous. Highly preferred crystalline aluminosilicate ion exchange materials contain from about 18% to about 22% water in their crystal matrix. The crystalline aluminosilicate ion exchange materials are further characterized by a particle size diameter of from about 0.1 micron to about 10 microns. Amorphous materials are often smaller, e.g., down to less than about 0.01 micron. Preferred ion exchange materials have a particle size diameter of from about 0.2 micron to about 4 microns. The term "particle size diameter" herein represents the average particle size diameter of a given ion exchange material as determined by conventional analytical techniques such as, for example, microscopic determination utilizing a scanning electron microscope. The crystalline aluminosilicate ion exchange materials herein are usually further characterized by their calcium ion exchange capacity, which is at least about 200 mg. equivalent of $CaCO_3$ water hardness/gm. of aluminosilicate, calculated on an anhydrous basis, and which generally is in the range of from about 300 mg.eq./g. to about 352 mg. eq./g. The aluminosilicate ion exchange materials herein are still further characterized by their calcium ion exchange rate which is at least about 2 grains $Ca++$/gallon/minute/gram of aluminosilicate (anhydrous basis), and generally lies within the range of from about 2 grains/gallon/minute/gram to about 6 grains/gallon/minute/gram, based on calcium ion hardness. Optimum aluminosilicate for builder purposes exhibit a calcium ion exchange rate of at least about 4 grains/gallon/minute/gram.

The amorphous aluminosilicate ion exchange materials usually have a Mg++ exchange capacity of at least about 50 mg. eq. CaCO$_3$/g(12 mg. Mg++/g.) and a Mg++ exchange rate of at least about 1 gr./gal./min./g./gal. Amorphous materials do not exhibit an observable diffraction pattern when examined by Cu radiation (1.54 Angstrom Units).

Aluminosilicate ion exchange materials useful in the practice of this invention are commercially available. The aluminosilicates useful in this invention can be crystalline or amorphous in structure and can be naturally-occurring aluminosilicates or synthetically derived. A method for producing aluminosilicate ion exchange materials is discussed in U.S. Pat. No. 3,985,669, issued Oct. 12, 1976, incorporated herein by reference. Preferred synthetic crystalline aluminosilicate ion exchange materials useful herein are available under the designation Zeolite A, Zeolite B, and Zeolite X.

Suitable alkali metal silicates have a mole ratio of SiO$_2$:alkali metal oxide in the range of from about 1:1 to about 4:1. The alkali metal silicate suitable herein include commercial preparations of the combination of silicon dioxide and alkali metal oxide or carbonate fused together in varying proportions according to, for example, the following reaction:

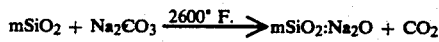

$$mSiO_2 + Na_2CO_3 \xrightarrow{2600°\ F.} mSiO_2:Na_2O + CO_2$$

The value of m, designating the molar ratio of SiO$_2$:Na$_2$O, ranges from about 0.5 to about 4 depending on the proposed use of the sodium silicate. The term "alkali metal silicate" as used herein refers to silicate solids with any ratio of SiO$_2$ to alkali metal oxide. Silicate solids normally possess a high alkalinity content; in addition water of hydration is frequently present as, for example, in metasilicates which can exist having 5, 6, or 9 molecules of water. Sodium silicate solids with a SiO$_2$:Na$_2$O mole ratio of from about 1.5 to about 3.5, are preferred in granular laundry detergent compositions.

Silicate solids are frequently added to granular detergent compositions as corrosion inhibitors to provide protection to the metal parts of the washing machine in which the detergent composition is utilized. Silicates have also been used to provide a degree of crispness and pourability to detergent granules which is very desirable to avoid lumping and caking.

Alkali metal carbonates are useful in the granular compositions of the invention as a source of washing solution alkalinity and because of the ability of the carbonate ion to remove calcium and magnesium ions from washing solutions by precipitation.

Preferred granular compositions free of inorganic phosphates contain from about 10% to about 40% by weight sodium carbonate, from 0% to about 30% sodium aluminosilicate, from about 0.5% to about 10% sodium silicate solids, from about 5% to about 35% of the ether hydroxypolycarboxylate metal sequestering agent compounds of the invention and from about 10% to about 25% surfactant.

Preferred liquid compositions free of inorganic phosphates contain from about 8% to about 20% by weight of non-soap anionic surfactants, from about 2% to about 18% ethoxylated nonionic surfactants, from about 5% to about 20% of a C$_{8-24}$ alkyl or alkenyl mono- or dicarboxylic acid or salt thereof and from about 2% to about 15% of the ether hydroxypolycarboxylate metal sequestering agent compounds of the invention.

ADDITIONAL OPTIONAL COMPONENTS

Granular compositions of this invention can contain materials such as sulfates, borates, perborates organic peroxy acid salts, peroxy bleach activators and water of hydration.

Liquid compositions of this invention can contain water and other solvents. Low molecular weight primary or secondary alcohol exemplified by methanol, ethanol, propanol, and isopropanol are suitable. Monohydric alcohols are preferred for solubilizing the surfactant but polyols containing from 2 to about 6 carbon atoms and from 2 to about 6 hydroxy groups can be used and can provide improved enzyme stability. Examples of polyols include propylene glycol, ethylene glycol, glycerine and 1,2-propanediol. Ethanol is a particularly preferred alcohol.

The compositions of the invention can contain such materials as proteolytic and amylolytic enzymes, fabric whiteners and optical brighteners, sudsing control agents, hydrotropes such as sodium toluene or xylene sulfonate, perfumes, colorants, opacifiers, anti-redeposition agents and alkalinity control or buffering agents such as monoethanolamine and triethanolamine. The use of these materials is known in the detergent art.

Materials that provide clay soil removal/anti-redeposition benefits can also be incorporated in the detergent compositions of the invention and are particularly useful in liquid compositions of the invention.

These clay soil removal/anti-redeposition agents are usually included at levels of from about 0.1% to about 10% by weight of the composition.

One group of preferred clay soil removal/anti-redeposition agents are the ethoxylated amines disclosed in European Patent Application No. 112,593 of James M. Vander Meer, published July 4, 1984, incorporated herein by reference. Another group of preferred clay soil removal/anti-redeposition agents are the cationic compounds disclosed in European Patent Application No. 111,965 to Young S. Oh and Eugene P. Gosselink, published June 27, 1984, incorporated herein by reference. Other clay soil removal/anti-redeposition agents which can be used include the ethoxylated amine polymers disclosed in European Patent Application No. 111,984 to Eugene P. Gosselink, published June 27, 1984; the zwitterionic compounds disclosed in European Patent Application No. 111,976 to Donn N. Rubingh and Eugene P. Gosselink, published June 27, 1984; the zwitterionic polymers disclosed in European Patent Application No. 112,592 to Eugene P. Gosselink, published July 4, 1984; and the amine oxides disclosed in U.S. application Ser. No. 516,612 to Daniel S. Connor, filed July 22, 1983, all of which are incorporated herein by reference. Polyethylene glycol can also be incorporated to provide anti-redeposition and other benefits.

Soil release agents, such as disclosed in the art to reduce oily staining of polyester fabrics, are also useful in the compositions of the invention. U.S. Pat. No. 3,962,152 issued June 8, 1976, to Nicol et al., incorporated herein by reference, discloses copolymers of ethylene terephthalate and polyethylene oxide terephthalate as soil release agents. U.S. Pat. No. 4,174,305 issued Nov. 13, 1979, to Burns et al., incorporated herein by reference, discloses cellulose ether soil release agents. U.S. Ser. No. 684,511, filed Dec. 21, 1984, by Gosselink, incorporated herein by reference, discloses block polyester compounds useful as soil release agents in detergent compositions.

The detergent compositions of the invention can also include a bleach system comprising an inorganic or organic peroxy bleaching agent and, in preferred compositions, an organic peroxy acid bleach precursor.

Suitable inorganic peroxygen bleaches include sodium perborate mono- and tetrahydrate, sodium percarbonate, sodium persilicate and urea-hydrogen peroxide addition products and the clathrate $4Na_2SO_4:2H_2O_2$:-1NaCl. Suitable organic bleaches include peroxylauric acid, peroxyoctanoic acid, peroxynonanoic acid, peroxydecanoic acid, diperoxydodecanedioic acid, diperoxyazelaic acid, mono- and diperoxyphthalic acid and mono- and diperoxyisophthalic acid. The bleaching agent is generally present in the compositions of the invention at a level of from about 5% to about 35% preferably from about 10% to about 25% by weight.

The compositions of the invention preferably also contain an organic peroxy acid bleach precursor at a level of from about 0.5% to about 10%, preferably from about 1% to about 6% by weight. Suitable bleach precursors are disclosed in UK-A-2040983, and include for example, the peracetic acid bleach precursors such as tetraacetylethylenediamine, tetraacetylmethylenediamine, tetraacetylhexylenediamine, sodium p-acetoxybenzene sulfonate, tetraacetylglycouril, pentaacetylglucose, octaacetyllactose, and methyl o-acetoxy benzoate. Highly preferred bleach precursors, however, have the general formula

wherein R is an alkyl group containing from 6 to 12 carbon atoms wherein the longest linear alkyl chain extending from and including the carboxyl carbon contains from 5 to 10 carbon atoms and L is a leaving group, the conjugate acid of which has a logarithmic acidity constant in the range from 6 to 13.

The alkyl group, R, can be either linear or branched and, in preferred embodiments, it contains from 7 to 9 carbon atoms. Preferred leaving groups L have a logarithmic acidity constant in the range from about 7 to about 11, more preferably from about 8 to about 10. Examples of leaving groups are those having the formula

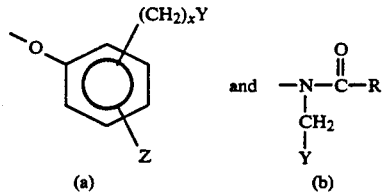

wherein Z is H, $R^1$ or halogen, $R^1$ is an alkyl group having from 1 to 4 carbon atoms, X is 0 or an integer of from 1 to 4 and Y is selected from $SO_3M$, $OSO_3M$, $CO_2M$, $N^+(R^1)_3O^-$ and $N^+(R^1)_2$-$O^-$ wherein M is H, alkali metal, alkaline earth metal, ammonium or substituted ammonium, and O is halide or methosulfate.

The preferred leaving group L has the formula (a) in which Z is H, x is 0 and Y is sulfonate, carboxylate or dimethylamine oxide radical. Highly preferred materials are sodium 3,5,5-trimethylhexanoyloxybenzene sulfonate, sodium 3,5,5-trimethylhexanoyloxybenzoate, sodium 2-ethylhexanoyl oxybenzenesulfonate, sodium nonanoyl oxybenzene sulfonate and sodium octanoyl oxybenzenesulfonate, the acyloxy group in each instance preferably being p-substituted.

The bleach activator herein will normally be added in the form of particles comprising finely-divided bleach activator and a binder. The binder is generally selected from nonionic surfactants such as the ethoxylated tallow alcohols, polyethylene glycols, anionic surfactants, film forming polymers, fatty acids and mixtures thereof. Highly preferred are nonionic surfactant binders, the bleach activator being admixed with the binder and extruded in the form of elongated particles through a radial extruder as described in European Patent Application No. 62523. Alternatively, the bleach activator particles can be prepared by spray drying.

The following embodiments illustrate, but are not limiting of, detergent compositions of the present invention. All percentages herein are by weight unless indicated otherwise. Polyepoxysuccinic acid is abbreviated as PESA in these examples.

COMPOSITION EXAMPLE I

A granular detergent composition for household laundry use is as follows:

| Component | Wt. % |
| --- | --- |
| Sodium $C_{14}$–$C_{15}$ alkylsulfate | 13.3 |
| Sodium $C_{13}$ linear alkyl benzene sulfonate | 5.7 |
| $C_{12}$–$C_{13}$ alkylpolyethoxylate (2.5) | 1.0 |
| Sodium toluene sulfonate | 1.0 |
| PESA, sodium salt-n = 2(51%), n = 3(21%) n = 4(16%), n > 4(13%) | 25.0 |
| Sodium N—hydroxyethylethylenediaminetriacetate | 2.0 |
| Sodium polyacrylate (Avg. M.W. approx. 5000) | 2.0 |
| Sodium carbonate | 20.3 |
| Sodium silicate | 5.8 |
| Polyethylene glycol (Avg. M.W. approx. 8000) | 1.0 |
| Sodium sulfate, water and miscellaneous | Balance to 100% |

The components are added together with continuous mixing with sufficient extra water (about 40% total) to form an aqueous slurry which is then spray dried to form the composition.

In the composition of Example I the following substitutions are made:
(a) for N-hydroxyethylethylenediaminetriacetate, sodium salt
 (1) diethylenetriaminepentakis (methylenephosphonate), sodium salt
 (2) 1,2-dihydroxy-3,5-disulfobenzene, sodium salt
(b) for sodium polyacrylate (avg. M.W. approx. 5000) sodium salt of an acrylate/maleate copolymer (avg. M.W. approx. 9000) in which the acrylate/maleate weight ratio is approximately 7:3.

COMPOSITION EXAMPLE II

A liquid detergent composition for household laundry use is as follows:

| Component | Wt. % |
| --- | --- |
| Potassium $C_{14}$–$C_{15}$ alkyl polyethoxy (2.5) sulfate | 8.3 |
| $C_{12}$–$C_{14}$ alkyl dimethyl amine oxide | 3.3 |
| Potassium toluene sulfonate | 5.0 |
| Monoethanolamine | 2.3 |
| PESA, potassium salt-n = 2(8%), n = 3(10%), n = 4(13%), n > 4(69%) | 15.0 |
| Potassium salt of 1,2-dihydroxy-3,5-disulfobenzene | 1.5 |
| Potassium polyacrylate (avg. M.W. approx. 9000) | 1.5 |
| Water and miscellaneous | Balance |

| Component | Wt. % |
|---|---|
|  | to 100% |

The components are added together with continuous mixing to form the composition.

COMPOSITION EXAMPLE III

A liquid detergent composition for household laundry use is prepared by mixing the following ingredients:

| | |
|---|---|
| $C_{13}$ alkylbenzenesulfonic acid | 10.5 |
| Triethanolamine cocoalkyl sulfate | 4.0 |
| $C_{14-15}$ alcohol ethoxy-7 | 12.0 |
| $C_{12-18}$ alkyl monocarboxylic acids | 15.0 |
| PESA, acid form-n = 2(20%), n = 3–4(35%), n = 3–6(70%), n > 6(10%) | 5.0 |
| Diethylenetriaminepentakis (methylenephosphonic) acid | 0.8 |
| Polyacrylic acid (avg. M.W. approx. 5000) | 0.8 |
| Triethanolamine | 4.5 |
| Ethanol | 8.6 |
| 1,2-Propanediol | 3.0 |
| Water, perfume, buffers and miscellaneous | Balance to 100% |

COMPOSITION EXAMPLE IV

In the Compositions which follow, the abbreviations used have the following designations:

| | |
|---|---|
| $C_{12}$LAS | Sodium linear $C_{12}$ benzene sulfonate |
| TAS | Sodium tallow alcohol sulfonate |
| $TAE_n$ | Hardened tallow alcohol ethoxylated with n moles of ethylene oxide per mole of alcohol |
| Dobanol 45$_E$7 | A $C_{14-15}$ primary alcohol condensed with 7 moles of ethylene oxide |
| TAED | Tetraacetyl ethylene diamine |
| NOBS | Sodium nonanoyl oxybenzenesulfonate |
| INOBS | Sodium 3,5,5 trimethyl hexanoyl oxybenzene sulfonate |
| Silicate | Sodium silicate having an $SiO_2:Na_2O$ ratio of 1:6 |
| Sulfate | Anhydrous sodium sulfate |
| Carbonate | Anhydrous sodium carbonate |
| CMC | Sodium carboxymethyl cellulose |
| Silicone | Comprising 0.14 parts by weight of an 85:15 by weight mixture of silanated silica and silicone, granulated with 1.3 parts of sodium tripolyphosphate, and 0.56 parts of tallow alcohol condensed with 25 molar proportions of ethylene oxide |
| PC1 | Copolymer of 3:7 maleic/acrylic acid, average molecular weight about 70,000, as sodium salt |
| PC2 | Polyacrylic acid, average molecular weight about 4,500, as sodium salt |
| PESA | Polyepoxysuccinic acid of formula HO—[CH(COOH)—CH(COOH)—O]$_n$—H n averaging about 10 (contains at least about 25% by weight where n = 2–4), M.W. (as Na salt, by NMR) = 950, Log $K_{Ca}$ = 5.3 |
| Perborate | Sodium perborate tetrahydrate of nominal formula $NaBO_2.3H_2O.H_2O_2$ |
| Enzyme | Protease |
| EDTA | Sodium ethylene diamine tetra acetate |
| Brightener | Disodium 4,4'-bis(2-morpholino-4-anilino-s-triazin-6-ylamino) stilbene-2:2'disulfonate |
| DETPMP | Diethylene triamine penta(methylene phosphonic acid), marketed by Monsanto under the Trade name Dequest 2060 |
| EDTMP | Ethylenediamine tetra (methylene phosphonic acid), marketed by Monsanto, under the Trade name Dequest 2041 |

Granular detergent compositions are prepared as follows. A base powder composition is first prepared by mixing all components except, where present, Dobanol 45E7, bleach, bleach activator, enzyme, suds suppressor, phosphate and carbonate in crutcher as an aqueous slurry at a temperature of about 55° C. and containing about 35% water. The slurry is then spray dried at a gas inlet temperature of about 330° C. to form base powder granules. The bleach activator, where present, is then admixed with $TAE_{25}$ as binder and extruded in the form of elongated particles through a radical extruder as described in European Patent Application No. 62523. The bleach activator noodles, bleach, enzyme, suds suppressor, phosphate and carbonate are then dry-mixed with the base powder composition and finally Dobanol 45E7 is sprayed into the final mixture.

| | COMPOSITIONS | | | |
|---|---|---|---|---|
| | A | B | C | D |
| $C_{12}$LAS | 4 | 9 | 8 | 8 |
| TAS | 4 | 3 | — | 3 |
| $TAE_{25}$ | 0.5 | 0.5 | 0.8 | — |
| $TAE_{11}$ | — | 1 | — | — |
| Dobanol 45E7 | 4 | — | 4 | 2 |

-continued

|  | COMPOSITIONS | | | |
|---|---|---|---|---|
|  | A | B | C | D |
| NOBS | — | 2 | — | — |
| INOBS | 3 | — | — | — |
| TAED | 0.5 | — | 3 | — |
| Perborate | 19 | 20 | 10 | 24 |
| EDTMP | 0.3 | — | 0.4 | 0.1 |
| DETPMP | — | 0.4 | — | — |
| EDTA | 0.2 | 0.2 | 0.2 | 0.1 |
| Magnesium (ppm) | 1000 | 1000 | 750 | — |
| PC1 | 2 | 1 | 2 | 2 |
| PC2 | 1 | 1 | — | 1 |
| PESA | 25 | 7 | 15 | 10 |
| Zeolite A* | — | 15 | 14 | — |
| Sodium tripolyphosphate | — | — | — | 12 |
| Coconut Soap | — | — | — | 2 |
| Carbonate | 17 | 15 | 10 | — |
| Silicate | 3 | 2 | 2 | 7 |
| Silicone | 0.2 | 0.2 | 0.3 | 0.2 |
| Enzyme | 0.8 | 0.5 | 0.4 | 0.3 |
| Brightener | 0.2 | 0.2 | 0.2 | 0.2 |
| Sulfate, Moisture & Miscellaneous | to 100 | | | |

*Zeolite A of 4 A pore size.

The above compositions are zero and low phosphate detergent compositions displaying excellent bleach stability, fabric care and detergency performance across the range of wash temperatures with particularly outstanding performance in the case of Compositions A, B and C on greasy and particulate soils at low wash temperatures.

What is claimed is:

1. Metal sequestering agent mixtures represented by the chemical structure

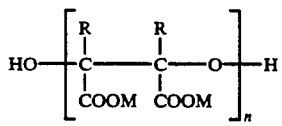

wherein M is hydrogen or a cation wherein the resultant salt is water soluble, each R is the same or different and is selected from hydrogen, $C_{1-4}$ alkyl or $C_{1-4}$ substituted alkyl and n is from about 2 to about 15, provided that at least about 25% by weight are compounds wherein n is from about 2 to about 4, and further provided that said mixtures have a log $K_{Ca}$ (35° C., 0.1M ionic strength) of at least about 4.5 at pH 9.5.

2. Mixtures according to claim 1 wherein n is from about 2 to about 10.

3. Mixtures according to claim 2 wherein the average n on a weight basis is from about 2 to about 4.

4. Mixtures according to claim 2 wherein M is alkali metal.

5. Mixtures according to claim 2 wherein R is hydrogen.

6. A detergent composition comprising from about 0.5% to about 98% by weight of a surfactant and from about 2% to about 99.5% by weight of metal sequestering agent mixtures represented by the chemical structure

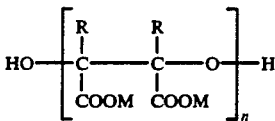

wherein M is hydrogen, alkali metal, ammonium or substituted ammonium, R is hydrogen, $C_{1-4}$ alkyl or $C_{1-4}$ substituted alkyl, and n is from about 2 to about 15, provided that at least about 25% by weight are compounds wherein n is from about 2 to about 4, and further provided that said mixtures have a log $K_{Ca}$ (35° C., 0.1M ionic strength) of at least about 4.5 at pH 9.5.

7. The composition of claim 6 which comprises from about 5% to about 30% by weight of a surfactant and from about 2% to about 50% by weight of said metal sequestering agent mixtures.

8. The composition of claim 6 in granular form which comprises from about 10% to about 25% by weight of a surfactant and from about 4% to about 50% by weight of said metal sequestering agent mixtures.

9. The composition of claim 6 in liquid form which comprises from about 10% to about 20% by weight of non-soap surfactants, from about 8% to about 20% by weight of $C_8$–$C_{24}$ mono- or di-carboxylic acids and from about 2% to about 15% by weight of said metal sequestering agent mixtures.

10. The composition according to claim 6 wherein M is alkali metal, R is hydrogen and n is from about 2 to about 10.

11. A composition according to claim 6 additionally comprising from about 5% to about 35% by weight of inorganic or organic peroxy bleaching agent.

12. A composition according to claim 11 additionally comprising from about 0.5% to about 10% by weight of organic peroxyacid bleach precursor.

13. A composition according to claim 12 wherein the bleach precursor has the general formula:

wherein R is an alkyl group containing from 6 to 12 carbon atoms wherein the longest linear alkyl chain extending from and including the carboxyl carbon contains from 5 to 10 carbon atoms and L is a leaving group, the conjugate acid of which has a logarithmic acidity constant in the range from 6 to 13.

14. A method of making ether hydroxypolycarboxylate metal sequestering agent compounds represented by the formula:

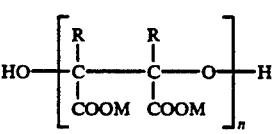

wherein M is hydrogen or a salt forming cation and n is from about 2 to about 15, which comprises: (1) treatment of an epoxysuccinate or an epoxysuccinate in admixture with a tartrate with at least about 5% of a molar equivalent of an alkaline calcium compound in aqueous media to form alkali metal and/or calcium salts of said ether hydroxypolycarboxylate sequestering agent compounds and (2) separation of said salts from the aqueous reaction media.

15. The method of claim 14 which comprises a subsequent ion exchange step such that M is H or alkali metal.

16. A method for laundering fabrics comprising the agitation of said fabrics in an aqueous solution containing from about 0.1% to about 1% of the composition of claim 6.

17. A method for laundering fabrics comprising the agitation of said fabrics in an aqueous solution containing from about 0.1% to about 1% of the composition of claim 10.

18. Mixtures prepared according to the method of claim 14.

* * * * *

UNITED STATES PATENT AND TRADEMARK OFFICE
CERTIFICATE OF CORRECTION

PATENT NO. : 4,654,159
DATED : March 31, 1987
INVENTOR(S) : Rodney D. Bush, Stephen W. Heinzman It is certified that error appears in the above-identified patent and that said Letters Patent are hereby corrected as shown below:

Column 6, line 32, "diluton" should be --dilution--.

Column 6, line 38, "liquid" should be --ligand--.

Column 8, line 31, "or" should be --of--.

Column 9, line 30, "thee" should be --the--.

Column 10, line 61, "Nov. 1, 1977)" should be --(Nov. 1, 1977)--.

Column 11, line 38, "$C-PO_3M_2$" should be -- $\rangle C-PO_3M_2$ --.

Signed and Sealed this

Thirtieth Day of August, 1988

Attest:

DONALD J. QUIGG

*Attesting Officer*  *Commissioner of Patents and Trademarks*